United States Patent
Kshirsagar et al.

(10) Patent No.: US 8,372,416 B2
(45) Date of Patent: Feb. 12, 2013

(54) PROCESS FOR LIMITING THE GROWTH OF MICROORGANISMS

(75) Inventors: Manjiri T. Kshirsagar, Woodbury, MN (US); Tushar A. Kshirsagar, Woodbury, MN (US); Thomas E. Wood, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 229 days.

(21) Appl. No.: 12/679,158

(22) PCT Filed: Oct. 1, 2008

(86) PCT No.: PCT/US2008/078413
§ 371 (c)(1),
(2), (4) Date: Mar. 19, 2010

(87) PCT Pub. No.: WO2009/046081
PCT Pub. Date: Apr. 9, 2009

(65) Prior Publication Data
US 2010/0247592 A1     Sep. 30, 2010

Related U.S. Application Data

(60) Provisional application No. 60/977,171, filed on Oct. 3, 2007.

(51) Int. Cl.
*A01N 25/08*      (2006.01)

(52) U.S. Cl. .......................... 424/409; 424/411

(58) Field of Classification Search .......................... None
See application file for complete search history.

(56) References Cited

U.S. PATENT DOCUMENTS

| | | | |
|---|---|---|---|
| 4,046,712 A | 9/1977 | Cairns et al. | |
| 4,618,525 A | 10/1986 | Chamberlain et al. | |
| 5,880,067 A | 3/1999 | Linkous | |
| 6,238,686 B1 | 5/2001 | Burrell et al. | |
| 6,248,733 B1 | 6/2001 | Landgrebe et al. | |
| 6,432,396 B1 | 8/2002 | Landgrebe et al. | |
| 6,569,520 B1 | 5/2003 | Jacobs | |
| 6,881,701 B2 | 4/2005 | Jacobs | |
| 7,087,249 B2 * | 8/2006 | Burrell et al. ................ | 424/618 |
| 2003/0150707 A1 | 8/2003 | Carmignani et al. | |
| 2004/0127353 A1 | 7/2004 | Wu | |
| 2005/0095189 A1 | 5/2005 | Brey et al. | |
| 2006/0188580 A1 | 8/2006 | Sacks | |
| 2010/0190171 A1 | 7/2010 | Kshirsagar et al. | |
| 2010/0209961 A1 | 8/2010 | Kshirsagar et al. | |
| 2010/0248214 A1 | 9/2010 | Kshirsagar et al. | |

FOREIGN PATENT DOCUMENTS

| | | |
|---|---|---|
| JP | 11-226420 | 8/1999 |
| JP | 2000095977 | 4/2000 |
| WO | WO 2006/074126 | 7/2006 |
| WO | WO 2009/026035 | 2/2009 |

OTHER PUBLICATIONS

Bae et al., "Evaluation of Murine Norovirus, Feline Calicivirus, Poliovirus, and MS2 as Surrogates for Human Norovirus in a Model of Viral Persistence in Surface Water and Groundwater", Applied and Environmental Microbiology, vol. 72, No. 2, pp. 477-484, Jan. 2008.
Elahifard et al., "Apatite-Coated Ag/AgBr/$TiO_2$ Visible-light Photocatalyst for Destruction of Bacteria", J.Am.Chem.Soc, 129, pp. 9552-9553, Apr. 2007.
Wise and Takeuchi, "High Dispersion Platinum Catalyst by RF Sputtering," Journal of Catalysis 83, 477-479 (1983).
Fu et al., "Anatase $TiO_2$ Nanocomposites for Antimicrobial Coatings," J. Phys. Chem. B 109, 8889-8898 (Mar. 2005).
Haruta, "Size- and support-dependency in the catalysis of gold", *Catalysis Today*, vol. 36, (*1997) pp. 153-166.

* cited by examiner

*Primary Examiner* — Michael G Hartley
*Assistant Examiner* — Robert Cabral
(74) *Attorney, Agent, or Firm* — Stephen L. Crooks

(57) ABSTRACT

A process for limiting the growth of microorganisms comprises (a) providing an antimicrobial agent comprising fine-nanoscale gold on a support medium comprising nanoparticulate titania, the fine-nanoscale gold having been deposited on the support medium by physical vapor deposition; and (b) contacting at least one microorganism with the antimicrobial agent.

8 Claims, 1 Drawing Sheet

PROCESS FOR LIMITING THE GROWTH OF MICROORGANISMS

STATEMENT OF PRIORITY

This application claims the priority of U.S. Provisional Application No. 60/977,171 filed Oct. 3, 2007, the contents of which are hereby incorporated by reference.

FIELD

This invention relates to processes for limiting the growth or presence of microorganisms such as viruses, bacteria, and fungi.

BACKGROUND

The potential for the presence of pathogenic bacteria, viruses, and fungi in biological fluids such as saliva, tears, blood, and lymph is of significant concern to health care workers and patients. Surfaces contaminated with bacteria, viruses, and fungi can facilitate the spread of infections. Additionally, the usefulness of valuable food and industrial products can be destroyed by the presence of bacteria and viruses. Methods for minimizing the transmission of pathogens (for example, in the home, in hospitals, and in day-care centers) are therefore important.

Microorganisms can be killed or rendered static by a number of physical and chemical methods. Physical methods include the application of heat and/or radiation. Chemicals that have been used to limit viral, fungal, and bacterial growth include alcohols (usually, 70 percent by volume aqueous ethyl or isopropyl alcohol); phenol and phenol derivatives such as hexachlorophene; formaldehyde; glutaraldehyde; ethylene oxide; ether; detergents; chlorhexidine gluconate; heavy metals such as silver, gold, copper, and mercury; organic compounds of mercury such as mercurochrome; and oxidizing agents such as hydrogen peroxide, iodine, hypochlorite, and chlorine.

Antibiotics, such as bacitracin, the cephalosporins, cycloserine, the penicillins, vancomycin, chloramphenicol, the erythromycins, the tetracyclines, the sulfonamides, and the aminoglycosides (such as streptomycin, neomycin, and gentamycin) have traditionally been defined as chemicals made by microorganisms that can kill bacteria. Antibiotics have no effect on viruses.

Semiconductor photocatalysts (for example, oxides of titanium, zirconium, zinc, tin, iron, tungsten, and molybdenum) have been used for the destruction (by photochemical oxidation) of organic contaminants in fluid media. Titanium dioxide has been widely investigated because of its chemical stability, suitable bandgap structure for ultraviolet/visible photoactivation, and its relatively low cost. Co-catalysts (for example, platinum, palladium, silver, and/or oxides and sulfides of these metals) have been added to titanium dioxide to increase its photocatalytic activity.

More recently, nanosize titanium dioxide particles have been utilized and have been capped with a variety of noble metals to improve their photocatalytic efficiency. Gold-capped titanium dioxide nanocomposites have been formed from a mixture of titanium dioxide solution and a gold salt (for example, $HAuCl_4$) by the reduction of gold on the surface of the titanium dioxide nanoparticles using chemical or photochemical reduction methods. Such nanocomposites have been dispersed in aqueous media and shown to inhibit microbial growth in the presence of light.

Each of the foregoing antimicrobial agents (as well as other known antimicrobials) has its own set of advantages and disadvantages. Some are toxic, costly, or otherwise impractical as routine disinfecting compounds. Some are unstable and become inactive over time. Some function such that the target microorganism develops resistance to the antimicrobial agent.

SUMMARY

Thus, particularly in view of the development of more virulent forms of certain pathogens, we recognize that there is a need for alternative, effective methods for limiting the growth of microorganisms (for example, methods of inactivating viruses and of limiting bacterial and fungal growth). Such methods will preferably be simple, effective against a variety of microorganisms, effective in the presence of other biological material, and/or effective for use in a variety of different environments.

Briefly, in one aspect, this invention provides a process for limiting the growth of microorganisms (for example, bacteria, fungi, yeasts, and viruses (including both non-enveloped viruses and enveloped viruses)). The process comprises (a) providing an antimicrobial agent comprising fine-nanoscale gold on a support medium comprising nanoparticulate titania, the fine-nanoscale gold having been deposited on the support medium by physical vapor deposition (more preferably, by physical vapor deposition in an oxidizing atmosphere); and (b) contacting at least one microorganism with the antimicrobial agent.

It has been discovered that the physical vapor deposition of fine-nanoscale gold (that is, gold bodies having all dimensions less than or equal to 5 nanometers (nm) in size) on nanoparticulate titania can produce a material that exhibits potent antimicrobial properties. The antimicrobial properties of the material can be surprisingly potent relative to those of corresponding materials comprising gold deposited on nanoparticulate titania by methods other than physical vapor deposition (for example, chemical or photochemical methods). The resulting material can be effective against a variety of microorganisms (for example, both gram-negative and gram-positive bacteria), in the presence of other biological material (for example, protein), and in a variety of different environments (for example, in restaurants, hospitals, and restrooms).

In addition, the material can be effective under a variety of different lighting conditions. Its inherent antimicrobial characteristics can enable it to function effectively at low light levels or even in the absence of light. Yet it can also exhibit photocatalytic antimicrobial activity, as its antimicrobial characteristics can be further enhanced through exposure to light (visible and/or ultraviolet).

The process of the invention is simple (requiring no complex equipment or procedures) and relatively cost-effective (since only a relatively small amount of gold is used and the resulting material, as long as its light exposure is limited and its contact with oils and other contaminants is minimized, does not appear to lose its effectiveness with use and can therefore be recycled). The process can also be relatively fast, with preferred embodiments killing or rendering static up to about 90 percent or more of the microorganisms present in a sample or on a surface in less than about 2 minutes. Thus, in at least some embodiments, the process can meet the above-cited need for alternative antimicrobial methods that are simple, effective against a variety of microorganisms, effective in the presence of other biological material, and/or effective for use in a variety of different environments.

In another aspect, this invention also provides a process for disinfecting a surface. The process comprises applying, to at least a portion of at least one surface, an antimicrobial agent comprising fine-nanoscale gold on a support medium comprising nanoparticulate titania, the fine-nanoscale gold having been deposited on the support medium by physical vapor deposition (more preferably, by physical vapor deposition in an oxidizing atmosphere).

BRIEF DESCRIPTION OF DRAWING

These and other features, aspects, and advantages of the present invention will become better understood with regard to the following description, appended claims, and accompanying drawing, wherein:

Figure 1:
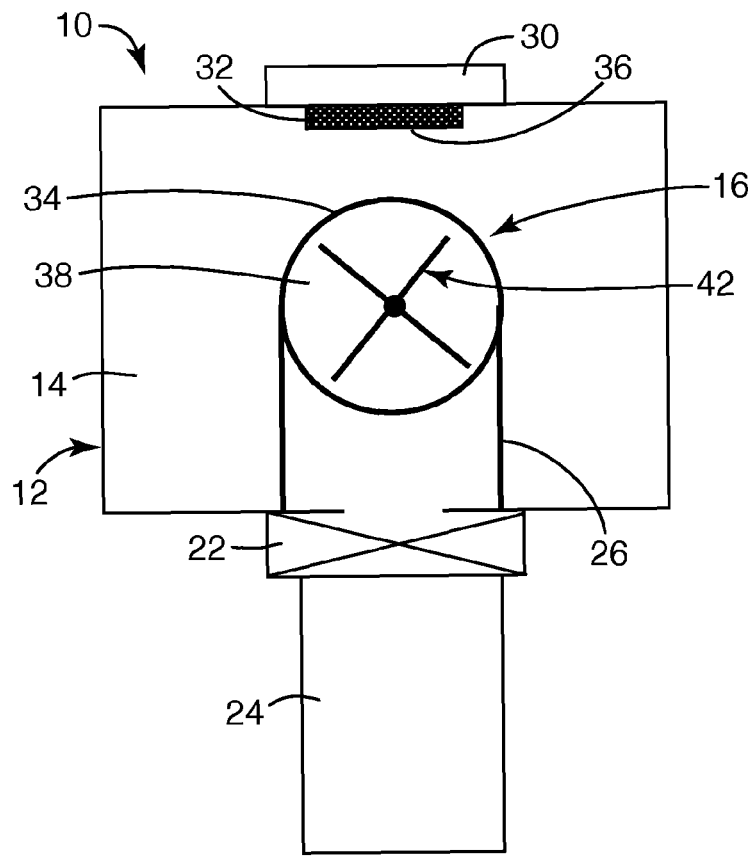
FIG. 1 shows, in side sectional view, an apparatus that was used in preparing antimicrobial agents for use in carrying out the embodiments of the process of the invention described in the examples section below.

These figures, which are idealized, are not drawn to scale and are intended to be merely illustrative and nonlimiting.

DETAILED DESCRIPTION

Definitions

As used in this patent application:

"contacting" includes direct physical contact of a microorganism with the antimicrobial agent used in the process of the invention, as well as indirect exposure of a microorganism to the antimicrobial agent (for example, via direct physical contact with a diffusible antimicrobial substance formed by the antimicrobial agent, which can mediate an antimicrobial effect on the microorganism without the need for direct physical contact with the antimicrobial agent itself);

"fine-nanoscale gold" means gold bodies (for example, particles or atom clusters) having all dimensions less than or equal to 5 nanometers (nm) in size;

"limiting the growth of a microorganism" means to inhibit, kill, prevent the replication of, or reduce the number of microorganisms present (thus, the term includes both "static" (that is, inhibiting growth or replication, but not necessarily killing; for example, bacteriostatic or fungistatic) and "cidal" (that is, killing; for example, bactericidal or fungicidal) activities);

"microorganism" means any cell having genetic material suitable for analysis or detection (including, for example, bacteria and viruses); and "target microorganism" means any microorganism that is desired to be limited in growth.

Antimicrobial Agent

The antimicrobial agents used in carrying out the process of the invention comprise fine-nanoscale gold on a support medium comprising nanoparticulate titania. The fine-nanoscale gold is or has been deposited on the support medium by physical vapor deposition (more preferably, by physical vapor deposition in an oxidizing atmosphere).

Gold

As used herein, the term "fine-nanoscale gold" refers to gold bodies (for example, particles or atom clusters) having all dimensions less than or equal to 5 nanometers (nm) in size. Preferably, antimicrobially active gold has all dimensions (for example, particle diameter or atom cluster diameter) in the range of up to (less than or equal to) about 5 nm in average size (more preferably, up to about 4 nm; even more preferably, up to about 3 nm). Most preferably, individual gold nanoparticles have a size of no more than about 2 nm in any dimension. Preferred embodiments can comprise gold nanoparticles that are at least about 0.1 nm in at least one dimension (more preferably, at least about 0.5 nm) and no greater than the above-described upper limits in any dimension.

In most preferred embodiments, at least a portion of the gold is ultra-nanoscale (that is, having at least two dimensions less than 0.5 nm in size and all dimensions less than 1.5 nm in size). The size of individual gold nanoparticles can be determined by transmission electron microscopy (TEM) analysis, as is well known in the art.

The amount of gold provided on a support medium can vary over a wide range. Since gold is expensive, it is desirable not to use more gold than is reasonably needed to achieve a desired degree of antimicrobial activity. Additionally, because nanoscale gold is highly mobile when deposited using PVD, activity can be compromised if too much gold is used, due to coalescence of at least some of the gold into large bodies.

For these reasons, the weight loading of gold on a support medium preferably is in the range of about 0.005 (more preferably, 0.05) to about 10 weight percent, more preferably about 0.005 (even more preferably, 0.05) to about 5 weight percent, and even more preferably from about 0.005 (most preferably, 0.05) to about 4.5 weight percent, based upon the total weight of the support medium and the gold.

Gold can be deposited by PVD techniques (for example, by sputtering) to form antimicrobially active, fine-nanoscale particles or atom clusters on a support surface. It is believed that the gold is deposited mainly in elemental form, although other oxidation states may be present. Although gold is mobile and will tend to accumulate in high energy sites of the surface, the nanoparticulate characteristics of the support apparently help to immobilize the gold and to keep the deposited gold particles and clusters isolated or discrete and preferably discontinuous. This can help to preserve activity that might otherwise be compromised if the gold were to coalesce into larger-sized bodies.

In addition to gold, one or more other metals can also be provided on the same supports and/or on other supports intermixed with gold-containing supports. Examples of such other metals include silver (preferred), palladium, platinum, rhodium, ruthenium, osmium, copper, iridium, and the like, and combinations thereof. If used, these other metals can be co-deposited on a support from a target source that is the same or different from the gold source target that is used. Alternatively, such metals can be provided on a support either before or after the gold is deposited. Metals requiring a thermal treatment for activation advantageously can be applied to a support and heat treated before the gold is deposited.

Support Medium

Support media suitable for use in preparing the antimicrobial agents include those that comprise nanoparticulate titania. As used herein, the term "nanoparticulate titania" means titania nanoparticles having an average diameter less than 50 nanometers (nm), where "diameter" refers not only to the diameter of substantially spherical particles but also to the longest dimension of non-spherical particles. Preferably, the nanoparticles have at least two dimensions less than or equal to about 30 nm in size (more preferably, less than or equal to about 15 nm; most preferably, less than or equal to about 10 nm). The support medium can optionally further comprise larger particles (for example, nanoparticles having an average diameter greater than 50 nm and less than 100 nm, or even larger particles) in minor amounts (that is, less than 50 percent of the total weight of the support medium; more preferably, less than about 20 percent; most preferably, less than about 10 percent).

The nanoparticulate characteristic of the support appears to aid in immobilizing gold deposited on the support surface, as smaller particle sizes of gold and higher activity can be observed using such supports. The titania nanoparticles of the support media are preferably associated in some manner to form agglomerates. For example, the nanoparticles can be associated physically (for example, through London forces or hydrogen bonding) or chemically (for example, through covalent or ionic bonding). The resulting agglomerates preferably have all dimensions in the range of about 0.1 micrometer to about 15 micrometers in average size. The agglomerates can be further assembled (for example, through spray drying, sol-gel processes, or coating, with or without the use of adhesion agents) to form agglomerate networks.

The agglomerates generally can be porous (even when formed from non-porous nanoparticles) due to the generally imperfect packing of the nanoparticles from which they are formed. Preferably, either the nanoparticles or the resulting agglomerates (or both) are porous. The agglomerates can be relatively robust (for example, when formed by sol-gel processes using nanoparticle sol precursors) or relatively friable (for example, when formed within a dry powder bed or by the drying of a dispersion of aggomerates in liquid). Sol-gel formation processes can include drying and/or thermal treatments, which can bond the nanoparticles together without removing the porosity created by imperfect packing of the nanoparticles in the intermediate gel.

Preferably, the support media have a porosity (that is, the volume ratio of pore space to the total volume of the support medium) greater than about 0.4 (preferably, greater than about 0.5). Porosities can be observed and measured via transmission electron microscopy (TEM).

More preferably, the support media are nanoporous (that is, have a porosity greater than about 0.4 and pore diameters ranging from about 1 nm to about 100 nm in size). Most preferably, the support media can have a total nanoporous capacity for pores in the size range of 1 to 10 nm that is greater than about 20 percent (that is, greater than about 0.20 using the formula below) of its total volume of pores in the size range of 1 to 100 nm, as calculated using the following formula (with data obtained, for example, by TEM):

$$NPC = \frac{CPv_1 - CPv_{10}}{CPv_1 - CPv_{100}}$$

wherein NPC refers to the total nanoporous capacity of the support medium; $CPv_n$ refers to the cumulative pore volume at pore radius n in cubic centimeters per gram ($cm^3/g$); and n is the pore radius in nanometers.

Preferred support media include those that are nanoporous in an exterior surface region of the support medium at a depth equal to or greater than the penetration depth of gold atoms deposited by PVD. Normally low surface area, non-nanoporous materials can be made to possess exterior surfaces characterized by nanoporosity by various methods (for example, by adsorption of nanoporous materials such as nanoparticle size colloids on the surface of a larger, host material to form a composite; by hydrolysis of metal alkoxides or metal salts on the surface of a material; and by oxidation of a thin film of metal on the surface of a material). In the latter case, the thin metal films can be deposited by PVD methods, and the oxidation can be carried out by dry or moist air to produce a nanoporous film on the material.

Useful support media can comprise various forms or shapes of support materials (for example, powders, particles, pellets, granules, extrudates, fibers, shells, honeycombs, plates, scrims, fabrics, paper, and the like, and combinations thereof). Particles can be regular in shape, irregular, dendritic, dendrite-free, or the like. Preferred supports include particles, powders, and combinations thereof.

In addition to the titania nanoparticles, particulate embodiments of support media can comprise particles of any of a wide range of particle sizes. For example, the titania nanoparticles and/or nanoparticle agglomerates can be combined with other particulate photocatalysts or antimicrobials, and/or with concentration agents (that is, known or hereafter-developed materials that can function to capture or immobilize microorganisms), to further modify the characteristics of the support media. Such additives can range in average size, for example, from less than about one-half to about ten times the average nanoparticle or nanoparticle agglomerate size. Often, however, the additives are comparable in average size to that of the nanoparticles or nanoparticle agglomerates.

Representative examples of materials useful (alone or in combination with other materials) as components of the support media include carbonaceous materials (for example, activated carbon, graphite, and the like), silicaceous materials (for example, silica, silica-titania (including mixtures of silica nanoparticles and titania nanoparticles, nanoparticles of an oxide comprising both silicon and titanium, and the like), silica-alumina, and the like), metal compounds (for example, metal oxides and the like), and the like, and combinations thereof. Useful metal oxides include oxides of one or more of cerium, aluminum, titanium, vanadium, chromium, manganese, cobalt, nickel, copper, zinc, gallium, yttrium, zirconium, niobium, molybdenum, iron, tin, antimony, lanthanum, tungsten, and combinations thereof. Oxides of one or more of calcium, potassium, sodium, magnesium, germanium, strontium, ruthenium, rhodium, palladium, silver, indium, barium, hafnium, thallium, rhenium, platinum, and combinations thereof also can be useful in admixture with one or more of the foregoing oxides.

Preferred materials for use (alone or in combination with other materials) as support media include titania, titania-alumina, titania-silica, and the like, and combinations thereof. Titania is commercially available in nanoparticulate form. Titania is more preferred (most preferably, at least a portion of the titania being in the anatase crystalline form).

Particle size of the components of the above-described support media can be measured in any appropriate manner in accordance with conventional practices now or hereafter practiced. For example, the average diameter of nanoparticles can be determined by inspection of TEM information, the average diameter of nanoparticle agglomerates in the range of about 0.1 micrometer to about 25 micrometers can be determined through scanning electron microscopy (SEM), and the average diameter of larger (than about 5 micrometer) particles or agglomerates can be determined by optical microscopy.

Deposition Process

Physical vapor deposition refers to the physical transfer of gold from a gold-containing source or target to a support medium. Physical vapor deposition can be viewed as involving atom-by-atom deposition, although in actual practice the gold can be transferred as extremely fine bodies constituting more than one atom per body. The deposited gold can interact with the surface of the support medium physically, chemically, ionically, and/or otherwise.

Physical vapor deposition preferably occurs under temperature and vacuum conditions in which gold is quite mobile and will tend to migrate on the surface of the support medium until immobilized in some fashion (for example, by adhering to a site on or very near the support surface). Sites of adhering can include defects such as surface vacancies, structural discontinuities such as steps and dislocations, and interfacial boundaries between phases or crystals or other gold species such as small gold clusters. Gold deposited by PVD apparently is sufficiently immobilized that the gold can retain a high level of activity. In contrast, conventional methodologies often allow the gold to coalesce into such large bodies that activity can be compromised or even lost.

Physical vapor deposition can be carried out in various different ways. Representative approaches include sputter deposition (preferred), evaporation, and cathodic arc deposition. Any of these or other PVD approaches can be used in preparing the antimicrobial agents used in carrying out the process of the invention, although the nature of the PVD technique can impact the resulting activity.

For example, the energy of the physical vapor deposition technique can impact the mobility of the deposited gold and hence its tendency to coalesce. Higher energy tends to correspond to an increased tendency of the gold to coalesce. Increased coalescence, in turn, tends to reduce activity. Generally, the energy of the depositing species is lowest for evaporation, higher for sputter deposition (which can include some ion content in which a small fraction of the impinging metal species are ionized), and highest for cathodic arc deposition (which can include several tens of percents of ion content). Accordingly, if a particular PVD technique yields deposited gold that is more mobile than desired, it can be useful to use a PVD technique of lesser energy instead.

Physical vapor deposition preferably is performed while the support medium to be treated is being well-mixed (for example, tumbled, fluidized, milled, or the like) to ensure adequate treatment of support surfaces. Methods of tumbling particles for deposition by PVD are described in U.S. Pat. No. 4,618,525 (Chamberlain et al.), the description of which is incorporated herein by reference. For described methods specifically directed at catalysts see Wise, "High Dispersion Platinum Catalyst by RF Sputtering," Journal of Catalysis 83, 477-479 (1983) and U.S. Pat. No. 4,046,712 (Cairns et al.), the descriptions of which are incorporated herein by reference.

When carrying out PVD on fine particles or fine particle agglomerates (for example, less than about 10 micrometers in average diameter), the support medium is preferably both mixed and comminuted (for example, ground or milled to some degree) during at least a portion of the PVD process. This can assist in maintaining the separation and free flow of the particles or agglomerates during the deposition. In the case of fine particles or fine particle agglomerates, it can be advantageous for the mixing of the particles to be as vigorous and rapid as possible while still retaining controlled deposition of the gold.

Figure 2:
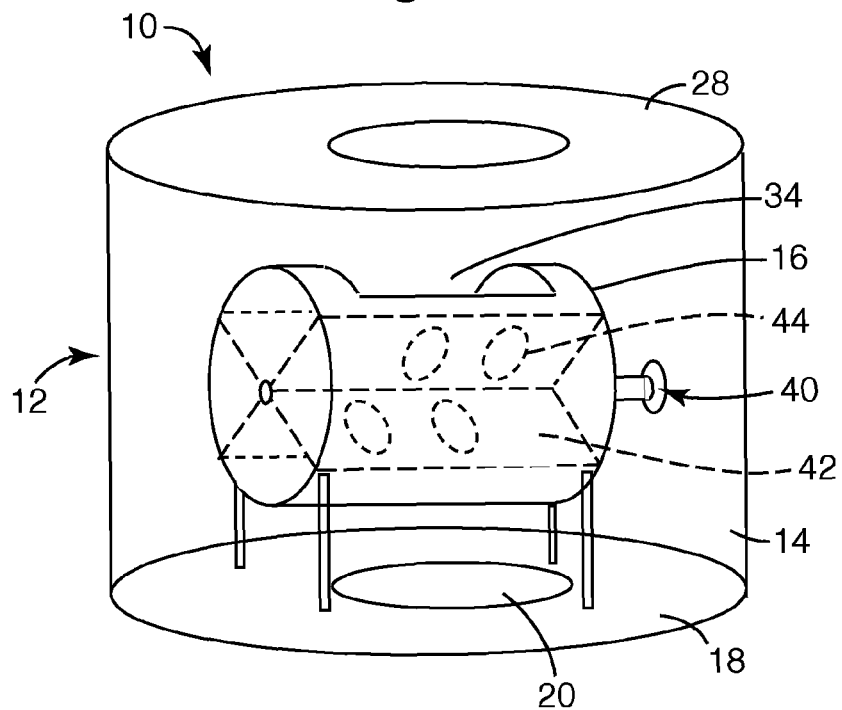
FIG. 2 shows, in perspective view, the apparatus of FIG. 1.

PVD can be carried out by using any of the types of apparatus that are now used or hereafter developed for this purpose. A preferred apparatus 10 is shown, however, in FIGS. 1 and 2. The apparatus 10 includes a housing 12 defining a vacuum chamber 14 containing a particle agitator 16. The housing 12, which can be made from an aluminum alloy if desired, is a vertically oriented hollow cylinder (for example, 45 cm high and 50 cm in diameter). The base 18 contains a port 20 for a high vacuum gate valve 22 followed by a six-inch diffusion pump 24 as well as a support 26 for the particle agitator 16. The vacuum chamber 14 is capable of being evacuated to background pressures in the range of $10^{-6}$ Torr.

The top of the housing 12 includes a demountable, rubber L-gasket-sealed plate 28 that is fitted with an external mount, three-inch diameter direct current (dc) magnetron sputter deposition source 30 (a US Gun II, US, INC., San Jose, Calif.). Into the sputter deposition source 30 is fastened a gold sputter target 32 (for example, 7.6 cm (3.0 inch) diameter× 0.48 cm (3/16 inch) thick). The sputter deposition source 30 is powered by an MDX-10 Magnetron Drive (Advanced Energy Industries, Inc, Fort Collins, Colo.) fitted with a Sparc-le 20 arc suppression system (Advanced Energy Industries, Inc, Fort Collins, Colo.).

The particle agitator 16 is a hollow cylinder (for example, 12 cm long×9.5 cm diameter horizontal) with a rectangular opening 34 (for example, 6.5 cm×7.5 cm). The opening 34 is positioned about 7 cm directly below the surface 36 of the gold sputter target 32, so that sputtered gold atoms can enter the agitator volume 38. The agitator 16 is fitted with a shaft 40 aligned with its axis. The shaft 40 has a rectangular cross section (for example, 1 cm×1 cm) to which are bolted four rectangular blades 42 which form an agitation mechanism or paddle wheel for the support particles being tumbled. The blades 42 each contain two holes 44 (for example, 2 cm diameter) to promote communication between the particle volumes contained in each of the four quadrants formed by the blades 42 and particle agitator 16. The dimensions of the blades 42 are selected to give side and end gap distances of either 2.7 mm or 1.7 mm with the agitator walls 48.

Physical vapor deposition can be carried out at essentially any desired temperature(s) over a very wide range. However, the deposited gold can be more active (perhaps due to more defects and/or lower mobility and coalescence) if the gold is deposited at relatively low temperatures (for example, at a temperature below about 150° C., preferably below about 50° C., more preferably at ambient temperature (for example, about 20° C. to about 27° C.) or less). Operating under ambient conditions can be generally preferred as being effective and economical, as no heating or chilling is required during the deposition.

The physical vapor deposition can be carried out in an inert sputtering gas atmosphere (for example, in argon, helium, xenon, radon, or a mixture of two or more thereof (preferably, argon)), but optionally the physical vapor deposition is carried out in an oxidizing atmosphere. The oxidizing atmosphere preferably comprises at least one oxygen-containing gas (more preferably, an oxygen-containing gas selected from oxygen, water, hydrogen peroxide, ozone, and combinations thereof; even more preferably, an oxygen-containing gas selected from oxygen, water, and combinations thereof; most preferably, oxygen). The oxidizing atmosphere further comprises an inert sputtering gas such as argon, helium, xenon, radon, or a mixture of two or more thereof (preferably, argon). The total gas pressure (all gases) in the vacuum chamber during the PVD process can be from about 1 mTorr to about 25 mTorr (preferably, from about 5 mTorr to about 15 mTorr). The oxidizing atmosphere can comprise from about 0.05 percent to about 60 percent by weight oxygen-containing gas (preferably, from about 0.1 percent to about 50 percent by weight; more preferably, from about 0.5 percent to about 25 percent by weight), based upon the total weight of all gases in the vacuum chamber.

Contacting

As used herein, "contacting" includes direct physical contact of a microorganism with the antimicrobial agent used in the process of the invention, as well as indirect exposure of a microorganism to the antimicrobial agent (for example, via direct physical contact with a diffusible antimicrobial substance formed by the antimicrobial agent, which can mediate an antimicrobial effect on the microorganism without the need for direct physical contact with the antimicrobial agent itself). The process of the invention can be carried out by any of various known or hereafter developed methods of providing such contact between two materials, and the antimicrobial agent can be used in any form that is amenable to providing such contact with a contaminated or contaminatable material or surface (for example, in particulate form or applied to a support such as a dipstick, film (for example, a reapplicable or repositionable film), filter, tube, well, plate, beads, membrane, or channel of a microfluidic device, or the like). Preferably, the antimicrobial agent is used in particulate form.

For example, the antimicrobial agent (alone or in combination with, for example, other antimicrobial materials or with carrier materials in the form of liquids (for example, water or oils), solids (for example, fabrics, polymers, papers, or inorganic solids), gels, creams, foams, or pastes) can be applied, coated, sprayed, dried onto, rubbed against, used as a dip for, impregnated into, or compounded with a non-porous or porous, solid, microorganism-contaminated or microorganism-contaminatable material, or can be added to a contaminated or contaminatable liquid (for example, directly or as a coating on a dipstick or filter). Binders, stabilizers, surfactants, polymer plasticizers, or other property modifiers can be utilized, if desired.

The antimicrobial agent can be applied to woven or nonwoven fabrics and can be combined with a variety of solids (for example, inorganic materials such as hydroxyapatite, silica, or glass) to inhibit, limit, reduce, and/or prevent virus, bacterial, or fungal contamination. The antimicrobial agent can be applied to disposable surfaces such as paper, tissues, cotton swabs, surgical wear, or drapes, as well as to a variety of absorbent and nonabsorbent materials. Preferred substrates include those that are at least partially light transmissive.

For example, the antimicrobial agent can be incorporated into cloth or paper carrier materials for use as antimicrobial wipes. The incorporation of the antimicrobial agent into fabrics or porous polymers advantageously can prevent degradation of the fibers or material and also can result in killing of infiltrated or sequestered bacteria and fungi within the fibers or material, as in air or water filters, for example.

The antimicrobial agent can be applied (for example, in the form of a paste comprising a carrier material) to solid surfaces to limit the growth of microorganisms. Thus, the agent can be used for surface sterilization or disinfection, for example, in home, day-care, industrial, and hospital settings, for cleansing toys, equipment, medical devices, work surfaces, surfaces in hospitals including bed rails, computer key boards, light switches, door knobs, and other surfaces known as fomites that can transmit infection. A variety of equipment, disposables, and devices such as sutures, bandages, hypodermic needles, face masks and respirators (for example, disposable and reusable), surgical drapes, medical apparel (for example, gowns, aprons, and the like), wound dressings and contact layers, surgical gauze, containers, and the like can be sterilized or disinfected using the process of the invention.

The antimicrobial agent, alone or in combination with one or more antimicrobial materials such as virucidal, bactericidal or static, and/or fungicidal or static agents (such as a polymixin, a penicillin, another antibiotic, a virucide (for example, amantadine), alcohols (for example, ethanol or isopropanol), quaternary ammonium compounds (for example, benzalkonium chloride), and/or a fungicide (for example, nystatin), can be applied to a surface or to a solid or liquid material to limit growth or prevent viral or bacterial or fungal contamination. Alternatively, the antimicrobial agent alone or in combination with one or more virucidal, bactericidal or static and/or fungicidal or static agents can be added directly to a solid or liquid that is virus-laden or bacteria-laden or contaminated with fungus.

The amount of antimicrobial agent, the degree of contact (between the antimicrobial agent and the contaminated or contaminatable material), and the period of contact time that is sufficient to limit the growth of the microorganisms in a particular material or environment will vary (depending upon the nature and form of the antimicrobial agent, the nature of any light exposure, the type(s) and loadings of microorganisms, and the nature and form of the material or environment) and can be readily determined by one skilled in the art. Contact times of about 1 to about 30 minutes (preferably, about 2 to about 15 minutes; more preferably, about 5 to about 10 minutes) can be useful. An "effective amount" of the antimicrobial agent refers to an amount that is sufficient to limit the growth of a microorganism. For example, 10 milligrams of antimicrobial agent can often effectively disinfect a 1 milliliter sample containing $10^3$ microorganism colony forming units (CFUs) in about 2 minutes. Lower microorganism loadings can be disinfected in less time and/or using less antimicrobial agent.

In carrying out the process of the invention, mixing (for example, agitation or stirring), rubbing, and/or incubation are optional but preferred, in order to increase microorganism contact with the antimicrobial agent. A preferred contacting method includes both mixing or rubbing (for example, for about 30 seconds to about 1 minute) and incubating (for example, for about 2 to about 30 minutes) a microorganism-containing material with antimicrobial agent. When the antimicrobial agent is in the form of a particulate and the microorganism-containing material is in the form of a fluid, the incubation step preferably includes mixing or rocking and is preferably followed by settling of the particulate (for example, for about 8 to about 10 minutes).

When a carrier material is utilized, preferred concentrations of the antimicrobial agent in the carrier material will vary depending upon use. A preferred concentration range can be from about 0.01 µg/mL to about 15 mg/mL, but the antimicrobial agent can be effective at lower concentrations.

Optional Process Steps

The antimicrobial properties of the antimicrobial agent can be enhanced when the agent is exposed to light. While not intending to limit the scope of the present invention, and although the mechanisms of action of the antimicrobial agent in inhibiting growth of bacteria, viruses, and fungi have not been fully elucidated, the currently available data are compatible with the agent acting, at least in part, as a catalyst (that is, the agent is not consumed) in the formation of reactive species (for example, various highly reactive oxygen-containing species) to cause destruction of microorganisms (for example, by oxidation). Regardless of the mechanisms involved, the agent used in the process of the invention is able to limit microorganism growth with or without light exposure. Advantageously, the antimicrobial agent is recyclable and can be re-used as an antimicrobial agent.

Thus, the process of the invention optionally can include light exposure (preferably, during at least a portion of the above-described contacting step and/or when dealing with relatively high levels of microorganism contamination). Such light exposure can include exposure from a directed light source or from ambient light. Preferably, the antimicrobial agent is exposed to light of wavelengths of at least about 200 nanometers (nm) and less than about 900 nm. More preferably, the light has a wavelength of at least about 400 nm and less than about 850 nm.

Convenient and sufficient light sources are those typically used for fluorescent lighting of laboratories and offices as well as light-emitting diode (LED) sources, incandescent sources, sunlight, and lasers. Light exposure can be, for example, continuous, pulsating, or periodic, and a range of intensities and durations of light exposure (for example, an irradiance of at least about 270 $\mu W/cm^2$ for about five minutes) can be used. Preferred exposure times will vary depending upon the amount of antimicrobial agent and the intensity and spectral properties of the light source.

Optionally, the process of the invention can further comprise segregation, separation, and/or recycling of the antimicrobial agent (for example, by gravitational settling or centrifuge-assisted settling of a particulate agent, followed by removal of the resulting supernatant or collection of the agent on a filter, column, membrane, or film or in a pouch) to enable its re-use. The process of the invention can be carried out manually (for example, in a batch-wise manner) or can be automated (for example, to enable continuous or semi-continuous processing).

Microorganisms

The growth of a variety of microorganisms can be limited by using the process of the invention, including, for example, bacteria, fungi, yeasts, viruses (including both non-enveloped viruses and enveloped viruses), and the like, and combinations thereof (preferably, bacteria, viruses, and combinations thereof; more preferably, bacteria). The process has utility in the growth limitation of pathogens, which can be important for food safety or for medical, environmental, or anti-terrorism reasons.

The process of the invention can be particularly useful in the growth limitation of pathogenic bacteria, as well as various yeasts, molds, and mycoplasmas (and combinations of any of these) to prevent their colonization, infection, and/or replication in a host material. A variety of bacteria potentially can be growth limited by the process including, for example, *Proteus vulgaris, Escherichia coli, Klebsiella pneumoniae, Staphylococcus aureus, Pseudomonas aeruginosa,* and *Salmonella* sp, as well as *Staphylococcus, Streptococcus, Corynebacterium,* and *Listeria* (gram-positive bacteria), *Neisseria, Enterobacteriaceae* (also called coliforms, including the genera *Escherichia, Salmonella, Shigella*), *Campylobacter,* and *Legionella* (gram-negative bacteria), and the like, and combinations thereof. The coliforms are gram-negative rods (bacilli) that colonize the intestinal tract of humans and other animals and are associated with disease.

The process of the invention can be particularly effective in limiting the growth of gram-negative and gram-positive bacteria (especially, *Salmonella enterica* (particularly *Salmonella enterica* subsp. *enterica serovar Typhimurium*) and *Staphylococcus aureus,* respectively, and combinations thereof) and non-enveloped viruses (for example, norovirus, poliovirus, hepatitis A virus, rhinovirus, and combinations thereof; especially, a human-infecting enteric virus for which *Escherichia coli* bacteriophage is a surrogate) and combinations thereof. Testing regimes to assess process effectiveness with other microorganisms can be readily generated without undue experimentation by those of ordinary skill in the art of microbiology, in view of clinical laboratory testing standards and manuals and the guidance provided below.

EXAMPLES

Objects and advantages of this invention are further illustrated by the following examples, but the particular materials and amounts thereof recited in these examples, as well as other conditions and details, should not be construed to unduly limit this invention.

Materials

All microorganism cultures were purchased from The American Type Culture Collection (ATCC, Manassas, Va.).

A comparative sample consisting of gold nanoparticles supported on titania was obtained from the World Gold Council, London, UK (Lot Number Au—$TiO_2$ #02-6). The sample was described by the manufacturer as being about 1.5 weight percent nanoparticulate gold (average gold particle size of 3.5 nm with a standard deviation of 0.91 nm). The catalyst was said to have been prepared by a deposition-precipitation method.

A comparative sample consisting of gold nanoparticles supported on $Fe_2O_3$ was obtained from the World Gold Council, London, UK (Lot Number Au—$Fe_2O_3$ #02-4). The sample was described by the manufacturer as being about 5 weight percent nanoparticulate gold (average gold particle size of 4.0 nm with a standard deviation of 0.94 nm). The catalyst was said to have been prepared by a coprecipitation method.

Hombikat UV-100 titania (average primary crystallite size less than 10 nm by Scherer method; average surface area greater than 250 $m^2/g$) was purchased from Sachtleben Chemie, Duisburg, Germany. 300 cubic centimeters (cc; 135 g) of the Hombikat UV-100 titania was dried at 150° C. for 24 hours. The resulting dried powder was loaded into the PVD apparatus described above in the detailed description having a particle agitator with a blade gap of 1.7 mm. A 7.62 cm diameter round gold target was employed. The vacuum chamber of the apparatus was then evacuated overnight to a background pressure of $1\times10^{-4}$ Torr. Argon sputter gas was admitted to the chamber at a flow rate of 100 sccm, and the gate valve opening to the vacuum (diffusion) pump was adjusted to 10 mTorr process pressure. Gold sputtering was initiated at a power level of 0.10 kW and carried out essentially as described above, using a blade rotation rate of 6 rpm. The duration of the sputtering was varied to provide different levels of deposited gold, and the resulting weight loss of the gold sputter target was measured to determine the percent by weight gold deposited on the titania support.

After the sputter coating was completed, the vacuum chamber was vented with air to ambient conditions, and the resulting gold-coated sample was removed from the PVD apparatus. The amount of gold that had been deposited on the sample was determined by weighing (both before and after the deposition process) the gold sputtering target that was utilized. In general, about 20 percent of the weight loss of the target represented gold deposited on the sample (based on inductively coupled plasma analysis).

A second sample of Hombikat UV-100 titania powder was calcined to 200° C. in air by heating to 200° C. over 2 hours and then holding the sample at 200° C. for 1 hour. A sample of this material (300 cc; 126 g) was dried at 150° C. for 24 hours. The resulting dried powder was sputtered with gold essentially as described in the preceding paragraphs, except that the sputter gas contained oxygen as well as argon. The flow rate of argon was kept at 100 sccm, and the flow rate of oxygen was kept at 5 sccm. The total gas pressure was 10 mTorr, and a sputter power of 0.12 kW was utilized. The resulting weight loss of the gold sputter target was 15.33 g.

To prepare the resulting gold-coated nanoparticle powder samples for transmission electron microscopy (TEM) examination, each powder was dispersed in methanol, and a small drop of the resulting dispersion was allowed to contact a TEM grid. Excess methanol was removed, and the resulting test sample was fully dried prior to examination.

Images were taken at various magnifications (50,000× and 100,000×) in a transmission electron microscope (TEM; H-9000 available from Hitachi High Technologies America, Pleasanton, Calif.) at 300 KV accelerating voltage using a Gatan CCD camera and Digital Micrograph software (Gatan Inc., Warrenton, Pa.). Representative regions (for example, regions selected wherein the interface of the catalytic surface was clearly displayed in a fashion perpendicular to the surface of the sample) were imaged. Numerous (for example, more than 10) interfacial regions were examined.

Gold nanoparticle number density was determined by TEM by counting the number of gold nanoparticles in a very thin sample section of measured area. To make this determination, sample areas were selected that were suitably thin (less than about 10 nm), and the areas were imaged at 200, 000× or higher. The number of clearly-defined gold nanoparticles having all dimensions less than or equal to 5 nm in size within a geometrically measured area were counted, and the number of nanoparticles observed per 100 nm$^2$ of area determined. The gold nanoparticle number density was defined as the number of nanoparticles counted in a 100 nm$^2$ area. The minimum area of examination for each determination was 300 nm$^2$.

TEM examination of the gold-coated samples showed that both samples contained fine-nanoscale gold as well as ultra-nanoscale gold. The average gold nanoparticle size for the sample prepared in an oxygen-containing atmosphere was 1.9 nm, and the average gold nanoparticle size for the sample prepared in argon alone was found to be 1.7 nm. Both samples were found to contain primarily nanoscale gold, with many regions having gold nanoparticle number densities greater than 5 nanoparticles per 100 nm$^2$.

The gold-coated titania powders were also examined by scanning electron microscopy (SEM). Test samples were prepared by sprinkling the powder onto an aluminum SEM stub that had been pre-treated with acrylic adhesive. SEM examination revealed that all the samples appeared to be essentially identical in morphology. The powders consisted primarily of 0.2 to 1.0 micron titania nanoparticle agglomerates, along with larger clusters of these agglomerates. The smaller agglomerates were composed of smaller particles that appeared to be about 0.05 to about 0.2 micrometers in size. The larger clusters of agglomerates ranged from about 2 to 25 microns in size. A lattice-work of pores was observed in all the agglomerates, large and small. In the case of the larger clusters of agglomerates, 0.1 to 1 micrometer pores were observed, which were created by the packing of the smaller agglomerates that made up the clusters. In the smaller agglomerates, pores were observed that were less than 0.1 micrometer in size.

Antimicrobial Activity Test Method

An isolated microorganism colony was inoculated into 5 mL BBL™ Trypticase™Soy Broth (Becton Dickinson, Sparks, Md.) and incubated at 37° C. for 18-20 hours. This overnight culture at ~10$^9$ colony forming units/mL was diluted in adsorption buffer (containing 5 mM KCl, 1 mM CaCl$_2$, 0.1 mM MgCl$_2$, and 1 mM K$_2$HPO$_4$) at pH 7.2 to obtain 10$^3$ microorganisms per mL dilution. A 1.1 mL volume of the microorganism dilution was added to labeled sterile 5 mL polypropylene tubes (BD Falcon™, Becton Dickinson, Franklin Lakes, N.J.) containing 10 mg of antimicrobial agent and mixed on a Thermolyne Maximix Plus™ vortex mixer (Barnstead International, Iowa). Each capped tube was incubated at room temperature (25° C.) for 15 minutes on a Thermolyne Vari Mix™ shaker platform (Barnstead International, Iowa). After the incubation, each tube was allowed to stand on the lab bench for 10 minutes to settle the antimicrobial agent. Control sample tubes containing 1.1 mL of the microorganism dilution without antimicrobial agent were treated in the same manner. The resulting settled antimicrobial agent and/or supernatant (and the control samples) were then used for analysis.

1 mL of the supernatant was removed and plated undiluted or, in some cases, diluted 1:10 in sterile Butterfield's Buffer solution (pH 7.2±0.2 phosphate buffer solution; VWR Catalog Number 83008-093, VWR, West Chester, Pa.) and plated on 3M™ Petrifilm™ Aerobic Count Plates culture medium (dry, rehydratable; 3M Company, St. Paul., MN) according to the manufacturer's instructions. The settled antimicrobial agent was re-suspended in 1 mL sterile Butterfield's Buffer solution and plated on 3M™ Petrifilm™ Aerobic Count Plates culture medium. Aerobic count was quantified using a 3M™ Petrifilm™ Plate Reader (3M Company, St. Paul., MN).

The above procedure was carried out both with and without light exposure (laboratory overhead fluorescent lighting). The testing for antimicrobial activity in the absence of light was carried out by wrapping the sample-containing test tubes with aluminum foil (Reynolds Wrap™ Heavy Duty, Reynolds Consumer Products, Richmond, Va.) and by also covering the Thermolyne Vari Mix™ shaker platform, 37° C. incubator (VWR Model 1575, VWR International, West Chester, Pa.), and plated 3M™ Petrifilm™ Aerobic Count Plates culture medium with additional foil. In addition, the fluorescent lights in the testing laboratory area were switched off.

Results were calculated using the following formula:

Percent Control=(number of CFUs from plated supernatant or plated re-suspended antimicrobial agent)/(number of CFUs from plated untreated control sample)×100 (where CFU=Colony Forming Unit, which is a unit of live or viable microorganisms)

Results were then reported in terms of percent antimicrobial activity or disinfection by the antimicrobial agent using the formula below:

Percent Antimicrobial Activity=100−Percent Control

Examples 1-4 and Comparative Examples 1-4

Using the above-described antimicrobial activity test method, 10 mg of gold-coated titania antimicrobial agent (prepared by physical vapor deposition in an argon atmosphere as described above, to provide a sample containing approximately 8 weight percent gold) and 10 mg of Hombikat UV-100 titania (without gold) were tested separately for antimicrobial activity against target microorganisms, the gram-negative bacterium *Salmonella enterica* subsp. *enterica* serovar *Typhimurium* (ATCC 35987) and the gram-positive bacterium *Staphylococcus aureus* (ATCC 6538). 100 percent antimicrobial activity was observed for the gold-coated titania antimicrobial agent (for both target microorganisms and both with light exposure and in the absence of light). For the Hombikat UV-100 titania, less than 10 percent antimicrobial activity was observed (for both target microorganisms and both with and without light exposure) (standard deviation less than 10 percent for all samples).

Examples 5-8

Using the above-described antimicrobial activity test method, 10 mg samples of gold-coated titania antimicrobial agent (prepared by physical vapor deposition in an argon atmosphere, as described above) were tested separately for antimicrobial activity against target microorganisms, the gram-negative bacterium *Salmonella enterica* subsp. *enterica serovar Typhimurium* (ATCC 35987) and the gram-positive bacterium *Staphylococcus aureus* (ATCC 6538) in the presence of biological material, 300 micrograms per mL of Bovine Serum Albumin (hereinafter, BSA; Sigma Purified Fraction V BSA, Sigma Chemicals, Catalog Number A3294-50G, St. Louis, Mo.; from a 10 mg/mL stock solution of BSA in sterile deionized water). 100 percent antimicrobial activity was observed, for both target microorganisms and both with light exposure and in the absence of light (standard deviation less than 10 percent for all samples).

Examples 9-13

Using the above-described antimicrobial activity test method, 10 mg samples of gold-coated titania antimicrobial agent (prepared by physical vapor deposition in an argon atmosphere, as described above) were tested separately for antimicrobial activity against the gram-negative bacterium *Salmonella enterica* subsp. *enterica serovar Typhimurium* (ATCC 35987) for 1, 2, 5, 10, and 15 minutes of contact time (incubation), respectively, under fluorescent lights. 100 percent antimicrobial activity was observed for contact times of at least 2 minutes and 99.57 percent for 1 minute (standard deviation less than 10 percent for all samples).

Examples 14-19

Using the above-described antimicrobial activity test method, various weights of gold-coated titania antimicrobial agent (prepared by physical vapor deposition in an argon atmosphere, as described above) per volume of microorganism-contaminated sample (1 mg/mL, 5 mg/mL, and 10 mg/mL, respectively) were tested separately for antimicrobial activity against the gram-negative bacterium *Salmonella enterica* subsp. *enterica serovar Typhimurium* (ATCC 35987). 100 percent antimicrobial activity was observed for all concentrations, both in the presence and in the absence of light (standard deviation less than 10 percent for all samples).

Examples 20-21

Using the above-described antimicrobial activity test method, 20 mg samples of gold-coated titania antimicrobial agent (prepared by physical vapor deposition in an argon atmosphere, as described above) were tested separately for antimicrobial activity against the gram-negative bacterium *Salmonella enterica* subsp. *enterica serovar Typhimurium* (ATCC 35987) at a concentration of $4 \times 10^4$ CFU per mL for 30 minutes of incubation. 99.98 percent and 100 percent antimicrobial activity was observed in the presence and the absence of light, respectively (standard deviation less than 10 percent for all samples).

Example 22 and Comparative Examples 5-8

Using the above-described antimicrobial activity test method, 10 mg of gold-coated titania antimicrobial agent (prepared by physical vapor deposition in an argon atmosphere, as described above; designated PVD-Au/TiO$_2$) and 10 mg samples of each of the above-described World Gold Council standard materials (gold on titania (designated WGC-Au/TiO$_2$) and gold on iron oxide (designated WGC-Au/Fe$_2$O$_3$), respectively) were tested separately for antimicrobial activity against the gram-negative bacterium *Salmonella enterica* subsp. *enterica serovar Typhimurium* (ATCC 35987). The results are shown in Table 1 below (where the number of CFUs surviving in the supernatant and in the settled test material were summed to give a total percent control value for each test material, and percent antimicrobial activity was calculated by subtracting the total percent control value from 100) (standard deviation less than 10 percent for all samples).

TABLE 1

| Example No. | Antimicrobial Agent | Light Exposure | Antimicrobial Activity (Percent) |
|---|---|---|---|
| C-5 | WGC-Au/FeO | Yes | 25 |
| C-6 | WGC-Au/TiO$_2$ | Yes | 23 |
| C-7 | WGC-Au/FeO | No | 28 |
| C-8 | WGC-Au/TiO$_2$ | No | 33 |
| 22 | PVD-Au/TiO$_2$ | No | 100 |

Examples 23-27

Using the above-described antimicrobial activity test method, a 10 mg sample of gold-coated titania antimicrobial agent (prepared by physical vapor deposition in an argon atmosphere, as described above) was tested for antimicrobial activity against the gram-negative bacterium *Salmonella enterica* subsp. *enterica serovar Typhimurium* (ATCC 35987) in the absence of light. The resulting supernatant (1 mL) was removed and plated as described above to provide a percent antimicrobial activity for Cycle 1 (which used "fresh" antimicrobial agent). To the resulting settled antimicrobial agent, 1 mL of fresh microorganism dilution was added, and the test method was repeated. This process was carried out for a total of five cycles, in order to test the effectiveness of recycled antimicrobial agent (Cycles 2-5). The results are shown in Table 2 below (based on plated supernatants) (standard deviation less than 10 percent for all samples).

TABLE 2

| Example No. | Cycle No. | Antimicrobial Agent | Light Exposure | Antimicrobial Activity (Percent) |
|---|---|---|---|---|
| 23 | 1 | Fresh | No | 100 |
| 24 | 2 | Recycled (1 X) | No | 100 |
| 25 | 3 | Recycled (2 X) | No | 91 |
| 26 | 4 | Recycled (3 X) | No | 88 |
| 27 | 5 | Recycled (4 X) | No | 85 |

Example 28

Using the above-described antimicrobial activity test method, 10 mg of gold-coated titania antimicrobial agent (prepared by physical vapor deposition in an argon atmosphere as described above, to provide a sample containing approximately 4.3 weight percent gold) was tested separately for antimicrobial activity against target microorganisms, the gram-negative bacterium *Salmonella enterica* subsp. *enterica serovar Typhimurium* (ATCC 35987) and the gram-positive bacterium *Staphylococcus aureus* (ATCC 6538). 100 percent antimicrobial activity was observed for the gold-coated titania antimicrobial agent (for both target microorganisms and both with light exposure and in the absence of light).

Example 29

Using the above-described antimicrobial activity test method, 10 mg of gold-coated titania antimicrobial agent (prepared by physical vapor deposition in an argon atmosphere as described above, to provide a sample containing approximately 1.6 weight percent gold) was tested for antimicrobial activity against the gram-negative bacterium *Salmonella enterica* subsp. *enterica serovar Typhimurium* (ATCC 35987). 100 percent antimicrobial activity was observed for the gold-coated titania antimicrobial agent (both with light exposure and in the absence of light).

Example 30

Using the above-described antimicrobial activity test method, 10 mg of gold-coated titania antimicrobial agent (prepared by physical vapor deposition in an oxidizing atmosphere comprising argon and oxygen essentially as described above, to provide a sample containing approximately 4 weight percent gold on Hombikat UV 100 titania that had been calcined to 200° C. for 1 hour) was tested for antimicrobial activity against the gram-negative bacterium *Salmonella enterica* subsp. *enterica serovar Typhimurium* (ATCC 35987). 100 percent antimicrobial activity was observed for the gold-coated titania antimicrobial agent (both with light exposure and in the absence of light).

Examples 31-34

Two different weights (20 mg and 50 mg, respectively) of gold-coated titania antimicrobial agent (prepared by physical vapor deposition in an argon atmosphere as described above, to provide a sample containing approximately 4.3 weight percent gold; designated PVD-Au/TiO$_2$) were tested separately for antimicrobial activity against the target non-enveloped, bacteria-infecting virus, *Escherichia coli* bacteriophage MS2 (ATCC 15597-B1; which is often used as a surrogate for various human-infecting, non-enveloped enteric viruses) in the presence and absence of light. A double layer agar method (described below) was used to assay for surviving *Escherichia coli* bacteriophage MS2 (ATCC 15597-B1) using *Escherichia coli* bacteria (ATCC 15597) as host.

*Escherichia coli* bacteriophage MS2 stock was diluted tenfold serially in sterile 1× adsorption buffer (containing 5 mM KCl, 1 mM CaCl$_2$, 0.1 mM MgCl$_2$, and 1 mM K$_2$HPO$_4$) at pH 7.2 to obtain 10$^3$ plaque forming units per milliliter (PFUs/mL). A 1.0 mL volume of the resulting bacteriophage dilution was added to a labeled sterile 5 mL polypropylene tube (BD Falcon™, Becton Dickinson, Franklin Lakes, N.J.) containing 20 mg or 50 mg of antimicrobial agent and mixed on a Thermolyne Maximix Plus™ vortex mixer (Barnstead International, Iowa). The capped tube was incubated at room temperature (25° C.) for 15 minutes on a Thermolyne Vari Mix™ shaker platform (Barnstead International, Iowa). After the incubation, the tube was allowed to stand on the lab bench for 10 minutes to settle the antimicrobial agent. Control sample tubes containing 1.0 mL of the bacteriophage dilution without antimicrobial agent were treated in the same manner. The resulting settled antimicrobial agent and/or supernatant (and the control samples) were then used for analysis.

100 microliters of the supernatant was removed and assayed for bacteriophage using the double layer agar method described below. An additional 800 microliters of supernatant was removed and discarded. One hundred microliters of the settled antimicrobial agent was also assayed for bacteriophage. Testing of these bacteriophage test samples was performed with light exposure and without light exposure, essentially as described above in the test method section.

Double Layer Agar Method:

A single colony of *Escherichia coli* bacteria (ATCC 15597) was inoculated into 25 mL sterile 3 weight percent tryptic soy broth (Bacto™ Tryptic Soy Broth, Becton Dickinson and Company, Sparks, Md.; prepared according to manufacturer's instructions) and incubated at 37° C. in a shaker incubator (Innova™ 44, New Brunswick Scientific Co., Inc., Edison, N.J.) set at 250 revolutions per minute (rpm) overnight. 750 microliters of this overnight culture was used to inoculate 75 mL sterile 3 weight percent tryptic soy broth. The resulting culture was incubated at 37° C. in the shaker incubator set at 250 rpm to obtain *Escherichia coli* cells in the exponential phase as measured by absorbance at 550 nm (absorbance values 0.3-0.6) using a SpectraMax M5 spectrophotometer (Molecular Devices, Sunnyvale, Calif.). The cells were incubated on ice until used for assay.

One hundred microliters of the above-described bacteriophage test samples were mixed with 75 microliters of the ice-incubated *Escherichia coli* (host bacteria) cells and incubated at room temperature (25° C.) for 5 minutes. The resulting samples were mixed with 5 mL sterile molten top agar (3 weight percent tryptic soy broth, 1.5 weight percent NaCl, 0.6 weight percent agar; prepared that day and maintained in a 48° C. waterbath). The mixture was then poured on top of bottom agar (3 weight percent tryptic soy broth, 1.5 weight percent NaCl, 1.2 weight percent agar) in petridishes. The molten agar component of the mixture was allowed to solidify for 5 minutes, and the petridishes or plates were inverted and incubated at 37° C. The resulting plaques were counted after overnight incubation, and the results were calculated using the following formula:

Percent Control=(Number of PFUs from plated antimicrobial agent)/(Number of PFUs from plated untreated control)× 100 (where PFU=Plaque Forming Unit, which is a unit of infectious bacteriophages).

Results (based on plated agent; shown in Table 3 below; standard deviation less than 10 percent for all samples) were then reported in terms of percent antimicrobial activity by the antimicrobial agent using the formula below:

Percent Antimicrobial Activity=100−Percent Control

TABLE 3

| Example No. | Antimicrobial Agent | Light Exposure | Antimicrobial Activity (Percent) |
| --- | --- | --- | --- |
| 31 | 20 mg PVD-Au/TiO2 | Yes | 85 |
| 32 | 20 mg PVD-Au/TiO2 | No | 88 |
| 33 | 50 mg PVD-Au/TiO2 | Yes | 94 |
| 34 | 50 mg PVD-Au/TiO2 | No | 94 |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A process comprising (a) providing an antimicrobial agent comprising fine-nanoscale gold on a support medium comprising nanoparticulate titania, said fine-nanoscale gold having been deposited on said support medium by physical vapor deposition; and (b) contacting at least one microorganism with said antimicrobial agent wherein said fine-nanoscale gold comprises gold bodies having all dimension less than or equal to 4 nanometers in size, and wherein said antimicrobial agent comprises 0.005 to 10 weight percent gold, based upon the total weight of said fine-nanoscale gold and said support medium.

2. The process of claim 1, wherein said physical vapor deposition is a technique selected from sputter deposition, evaporation, cathodic arc deposition, and combinations thereof.

3. The process of claim 1, wherein said physical vapor deposition is carried out in an oxidizing atmosphere.

4. The process of claim 3, wherein said oxidizing atmosphere comprises at least one oxygen-containing gas.

5. The process of claim 4, wherein said oxygen-containing gas is selected from oxygen, water, hydrogen peroxide, ozone, and combinations thereof.

6. The process of claim 1, wherein said support medium comprises titania nanoparticles having at least two dimensions less than or equal to 30 nanometers in size.

7. The process of claim 1, wherein said support medium comprises agglomerates of titania nanoparticles.

8. A process comprising applying, to at least a portion of at least one surface, an antimicrobial agent comprising fine-nanoscale gold on a support medium comprising nanoparticulate titania, said fine-nanoscale gold having been deposited on said support medium by physical vapor deposition wherein said fine-nanoscale gold comprises gold bodies having all dimension less than or equal to 4 nanometers in size, and wherein said antimicrobial agent comprises 0.005 to 10 weight percent gold, based upon the total weight of said fine-nanoscale gold and said support medium.

* * * * *

UNITED STATES PATENT AND TRADEMARK OFFICE
CERTIFICATE OF CORRECTION

PATENT NO. : 8,372,416 B2  
APPLICATION NO. : 12/679158  
DATED : February 12, 2013  
INVENTOR(S) : Manjiri T. Kshirsagar et al.

It is certified that error appears in the above-identified patent and that said Letters Patent is hereby corrected as shown below:

In the Specifications:

Column 12
Line 34, delete "Ton." and insert -- Torr. --, therefor.

Column 14
Lines 37-38, delete "microorganisms)" and insert -- microorganisms). --, therefor.

Signed and Sealed this
Fourteenth Day of May, 2013

Teresa Stanek Rea
*Acting Director of the United States Patent and Trademark Office*